United States Patent [19]

Nagai et al.

[11] Patent Number: 5,499,547
[45] Date of Patent: Mar. 19, 1996

[54] ACTUATOR

[75] Inventors: Shigekazu Nagai; Akio Saitoh; Toru Sugiyama, all of Ibaraki, Japan

[73] Assignee: SMC Kabushiki Kaisha, Tokyo, Japan

[21] Appl. No.: 193,053

[22] PCT Filed: Sep. 4, 1992

[86] PCT No.: PCT/JP92/01134

§ 371 Date: Mar. 4, 1994

§ 102(e) Date: Mar. 4, 1994

[87] PCT Pub. No.: WO93/05321

PCT Pub. Date: Mar. 18, 1993

[30] Foreign Application Priority Data

Sep. 4, 1991 [JP] Japan .................................. 3-224403
Jul. 23, 1992 [JP] Japan .................................. 4-197178

[51] Int. Cl.⁶ .................................................. F16H 25/22
[52] U.S. Cl. ........................ 74/89.15; 74/424.8 R; 108/20; 108/143; 384/50
[58] Field of Search ................ 74/89.15, 424.8 B, 74/424.8 R; 108/20, 143; 384/45, 50

[56] References Cited

U.S. PATENT DOCUMENTS

| 4,598,238 | 7/1986 | Scarhno | 74/424.8 R X |
| 4,693,131 | 9/1987 | Teramachi | 74/424.8 B |
| 4,916,963 | 4/1990 | Takei | 74/424.8 B |
| 4,934,202 | 6/1990 | Hikita et al. | 74/424.8 R X |

FOREIGN PATENT DOCUMENTS

| 60-155052 | 8/1985 | Japan . | |
| 60-245360 | 12/1985 | Japan . | |
| 61-164852 | 10/1986 | Japan . | |
| 62-233517 | 10/1987 | Japan . | 384/50 |
| 63-62657 | 4/1988 | Japan . | |
| 63-198857 | 12/1988 | Japan . | |
| 1-69962 | 5/1989 | Japan . | |
| 1-86663 | 6/1989 | Japan . | |
| 1-109258 | 7/1989 | Japan . | |

*Primary Examiner*—Allan D. Herrmann
*Attorney, Agent, or Firm*—Oblon, Spivak, McClelland, Maier & Neustadt

[57] ABSTRACT

A motor, a ball screw shaft, etc. are accommodated within a frame that forms an outer frame. Direct-acting guides are provided on both sides of a groove-shaped opening defined in the frame. The ball screw shaft is centrally disposed within the frame. A table slides along the direct-acting guides under the action of rotation of the ball screw shaft. The ball screw shaft has ball-screw splines formed over its entire length and both ends thereof supported by the motor and a bearing. The center of rotation of the ball screw shaft is brought into alignment with the centers of rotation of the motor and the bearing by balls inserted into the ball-screw splines.

7 Claims, 17 Drawing Sheets

ACTUATOR

TECHNICAL FIELD

The present invention relates to an actuator, and more specifically to an actuator wherein the actuator drive source and a further drive shaft used for a slider are coupled to one another with high accuracy.

BACKGROUND ART

Slider actuators, as well as other actuators for industrial, medical or public use applications for effecting controls such as linear and rotational movement control, force control, position control, pattern control, phase-plane profile control, non-linear control, compliance control, etc. using rotatable drive sources [such as a rotatable electric motor, a fluid-pressure rotatable motor (using air, hydraulic pressure, water pressure or the like), a fuel engine, a biological-organism principle motor (a flagellum motor)] or the like generally include a coupling or connecting means intended for coupling the drive source to a means for effecting linear or rotational movement.

Further, electrical, fluidic, chemical-substance and biochemical drive sources are generally united into a work module in a compact manner, with the actuator bodies or actuators being aggregated together with control drivers used for the drive sources and power sources (such as a generator, a compressor, a vacuum pump, a fuel battery, or a biological energy or chemical energy source). A CIM and FA system, or Virtual Reality/Artificial Reality system is used to attempt to construct a modular distributed/integrated system for the CIM and FA system, with the Virtual Reality/Artificial Reality system being incorporated therein. Further, the individual actuators include control, distribution and intelligent control devices (such as a sequencer having a communicating and radio-communication exchanging means), a power system (e.g., electrical, fluid, fuel, chemical energy substance and biological energy substance sources) and a signal system, all of which are incorporated in an arrangement for the respective modules, a bus system and actuators.

In the individual actuators referred to above, however, the coupling between a slider drive source and a drive shaft thereof cannot be easily performed with high accuracy. It is also difficult to make reduce the size of each actuator, since the interconnection between the drive source and the slider drive shaft are performed by coupling.

Further, a problem arises in that a distortion occur at each actuator body, depending on the guide structure of the slider.

DISCLOSURE OF THE INVENTION

Therefore, an object of the present invention is to minimize the need for adjustment and maintenance of a coupling means as much as possible. Further, another object of the present invention is to provide an actuator capable of improving the dynamic and static characteristics of a connecting means or the like by reducing the weight, noise, produced dust, and generated heat thereof, and thereby converting biochemical energy into kinetic energy with high efficiency.

In order to achieve the above objects, the present invention is characterized in that a feed screw shaft for converting the rotational motion of a motor into a linear motion is provided to displace a slider. The feed screw shaft has ball-screw splines formed over its entirety, and is constructed such that the center of rotation of the feed screw shaft is brought into alignment with the center of rotation of the motor and a bearing thereof, by fitting balls or strings into the ball-screw splines.

The present invention is also characterized in that the motor and the feed screw shaft are accommodated within a frame forming an outer frame.

The present invention is further characterized in that the frame has a groove-like opening defined therein, and direct-acting guides are provided in the vicinity of the opening.

The present invention is still further characterized in that grooves are provided on both sides of each of the direct-acting guides, and guides for guiding the slider are inserted into the grooves respectively.

The present invention is still further characterized in that the slider is slidably moved along the guides by rollers interposed therebetween.

The present invention is still further characterized in that a pulley gear, associated with a belt for converting a rotational motion into a linear motion, is formed integrally with a rotor of the motor to displace a slider attached to the actuator.

BEST MODE FOR CARRYING OUT THE INVENTION

An actuator according to the present invention will hereinafter be described in detail by preferred embodiments with reference to the accompanying drawings.

Figure 1:
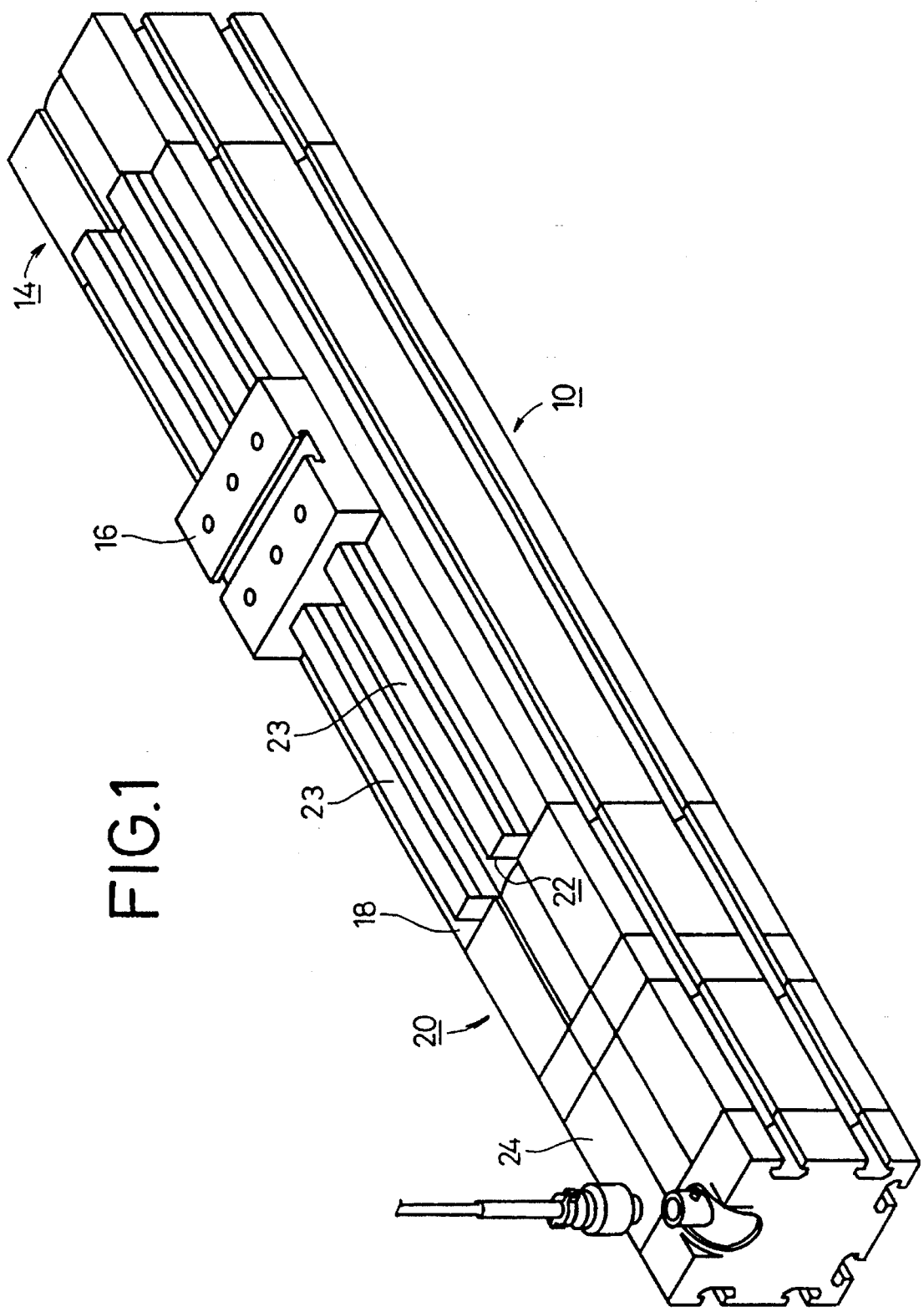
FIG. 1 is a perspective view showing an actuator according to a first embodiment of the present invention.
Figure 2:
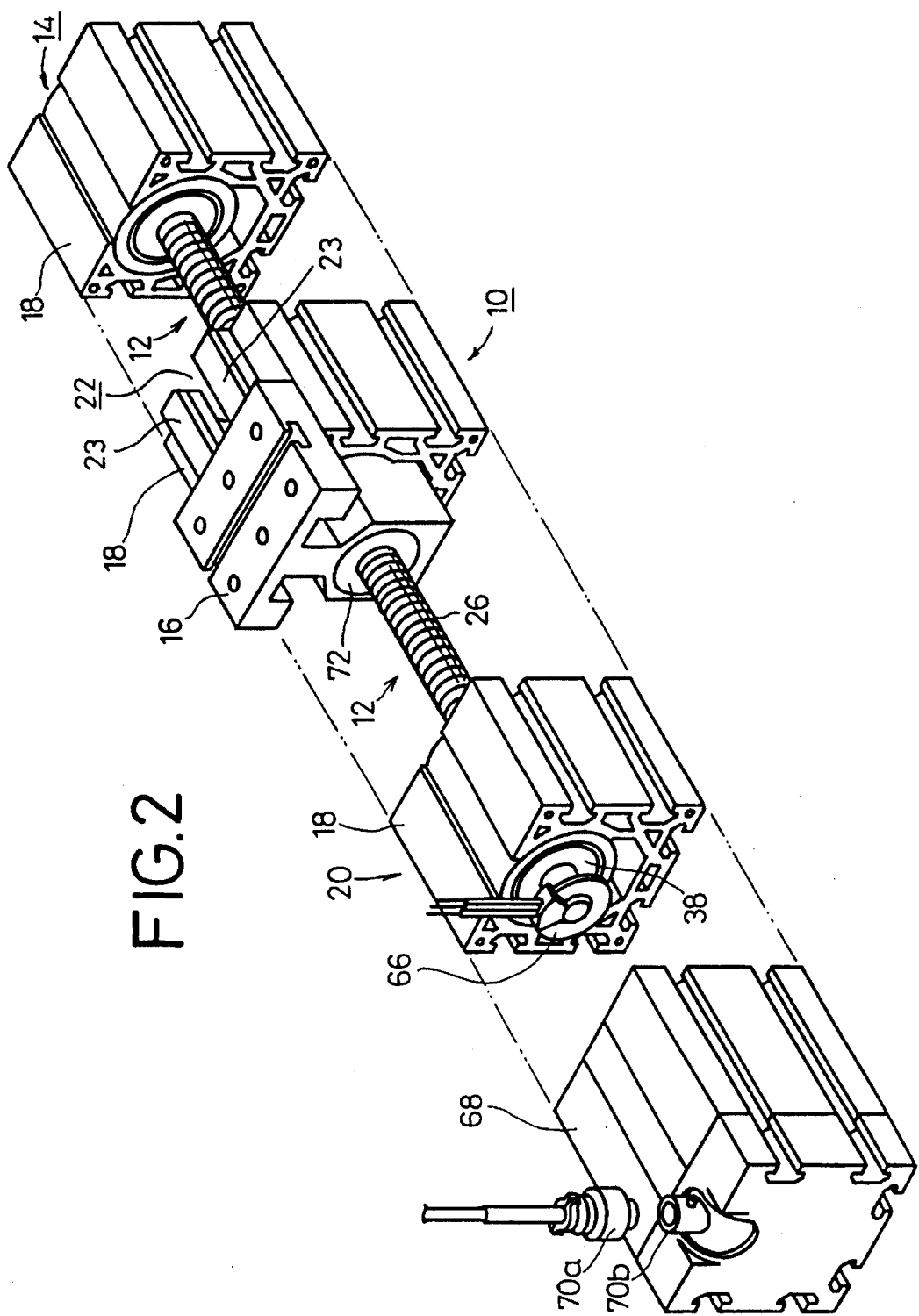
FIG. 2 is a partly-cut perspective view illustrating the actuator shown in FIG. 1.
Figure 3:
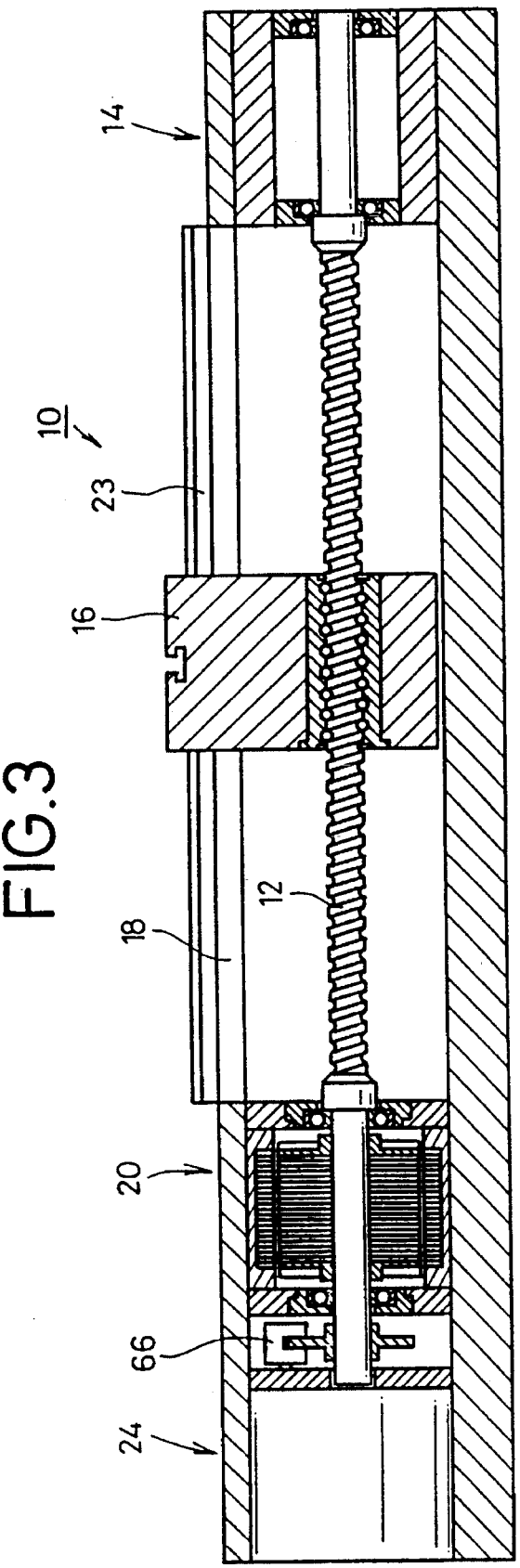
FIG. 3 is a partial cross-sectional view showing the actuator shown in FIG. 1.
Figure 4:
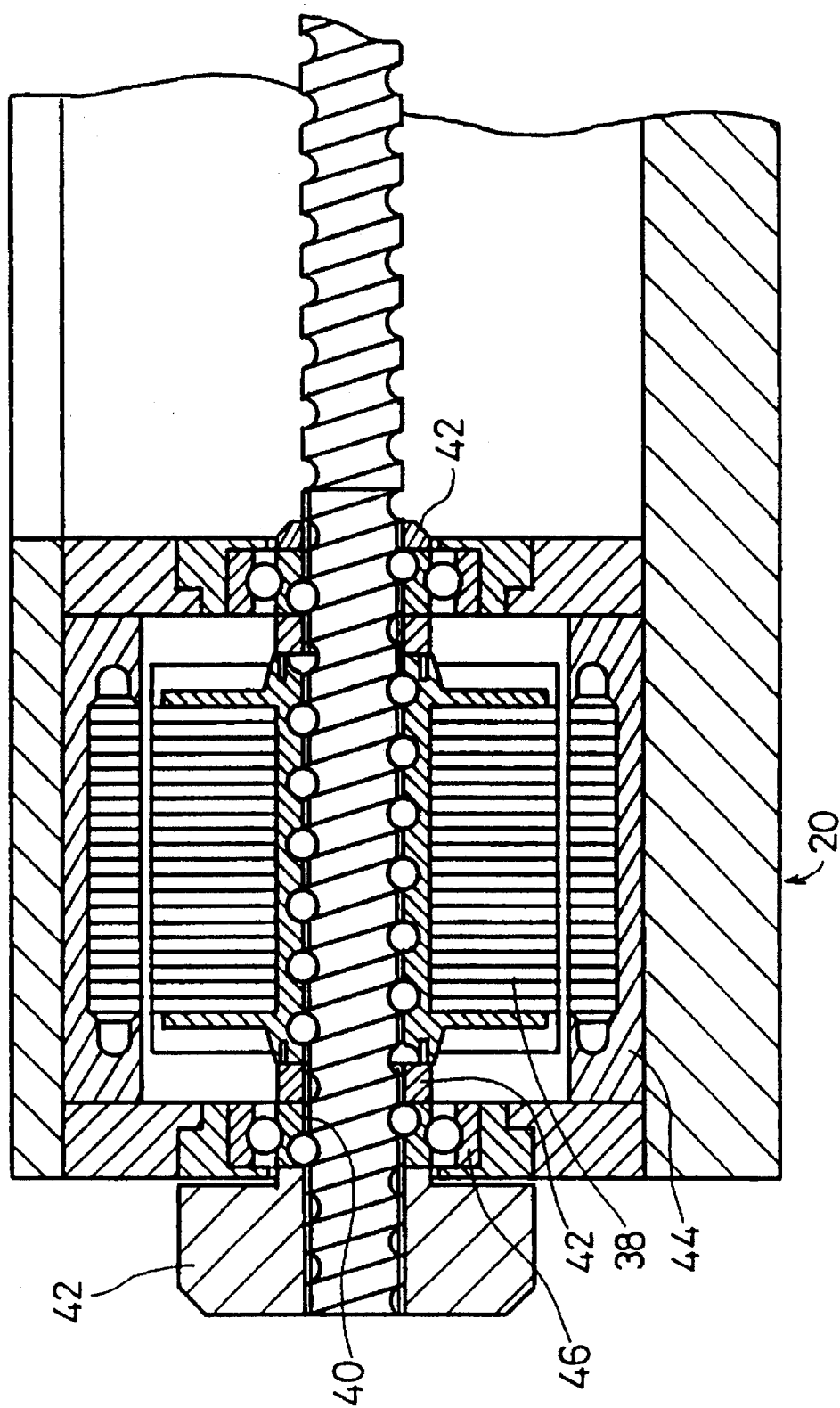
FIG. 4 is a cross-sectional view depicting a motor used for the actuator shown in FIG. 1.
Figure 5:
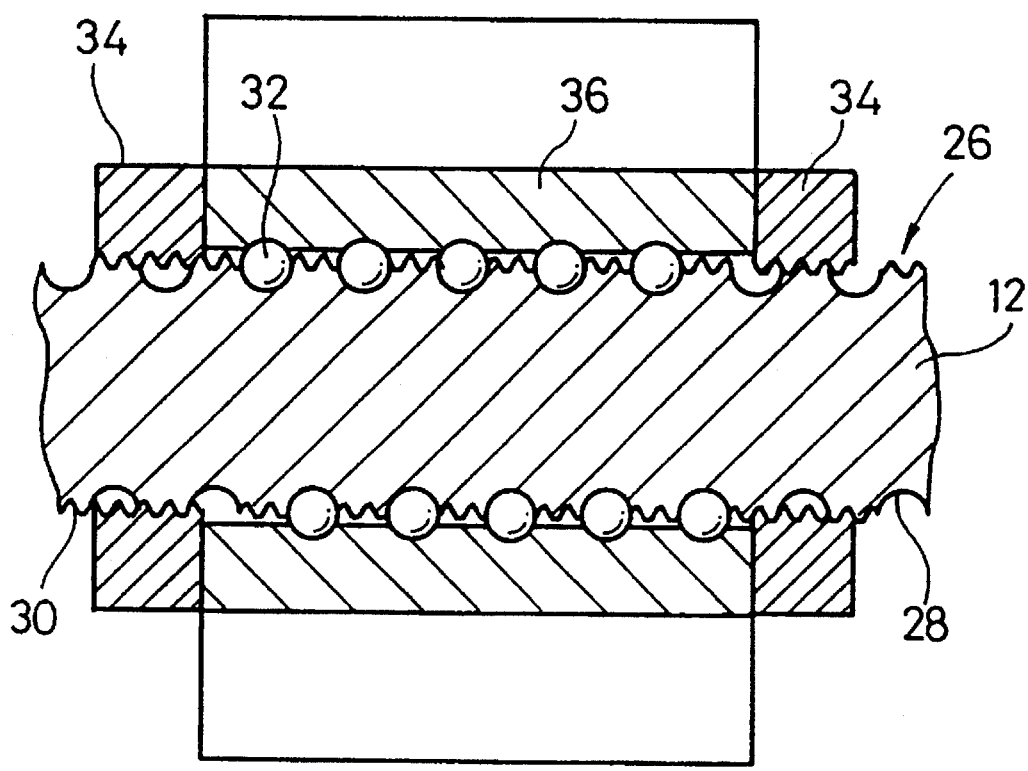
FIG. 5 is a cross-sectional view illustrating a bearing of the actuator shown in FIG. 1.
Figure 6:
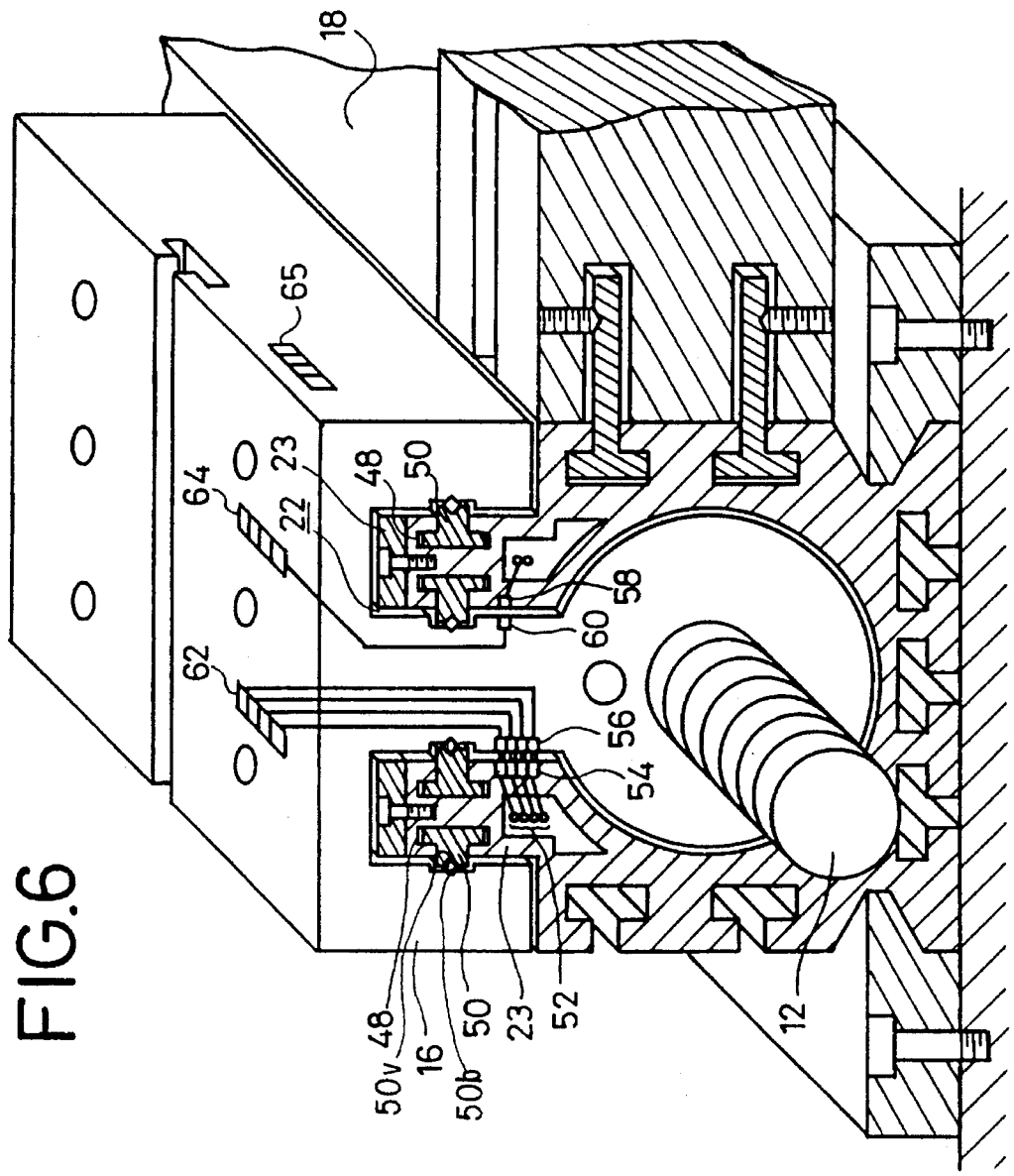
FIG. 6 is a perspective view showing another embodiment of an actuator according to the present invention, in which the relationship between a table employed in the embodiment and a body of the actuator is described.

FIG. 1 is a perspective view of an actuator according to a first embodiment. FIG. 2 is a partial perspective view of the actuator shown in FIG. 1. FIG. 3 is a partial vertical sectional view of the actuator shown in FIG. 1. FIG. 4 is a cross-sectional view of a motor used for the actuator shown in FIG. 3. FIG. 5 is a cross-sectional view of a bearing used for the actuator shown in FIG. 1. FIG. 6 is a perspective view of another embodiment in which the relationship between a table and an actuator body is described.

The actuator 10 according to the first embodiment is comprised principally of an actuator frame 18 (hereinafter called merely a "frame"), a table 16 movably disposed in the frame 18, a ball screw shaft 12 for driving the table 16, a motor 20 for rotating the ball screw shaft 12, a bearing 14, and a motor controller 24 using, for example, an inverter, of a type wherein programmable controllers (such as input, output, data-input, program-input, display, start, end and stop buttons and an emergency button) are integrally formed therein.

As shown in FIG. 2, the actuator 10 is constructed such that the frame 18 thereof forms an outer frame and holds or accommodates the motor 20, the ball screw shaft 12, etc. therein. A pair of direct-acting guides 23 is provided on both sides of a groove-like opening 22 centrally defined in the frame 18. Further, the ball screw shaft 12 is provided at the center of the frame 18, and the table 16 slides along the direct-acting guides 23 due to the rotating action of the ball screw shaft 12. The ball screw shaft 12 has ball-screw splines 26 formed over its entire length and both ends thereof supported by the motor 20 and the bearing 14.

Since the coincidence or concentricity between the axis of the ball screw shaft 12 and the axis of each of the ball-screw splines 26 is highly accurate as shown in FIG. 5, no special structural arrangement is required for supporting the ball screw shaft 12 by the bearing 14, or for producing the ball screw shaft 12. The support structure is constructed as follows: Male screws 30 are formed on the outer periphery of the ball-screw splines 26, and stoppers 34 are provided to fix the ball-screw splines 26 and a bearing 36. Since, in this case, the rolling contact surfaces of the ball screws are precisely concentric, they are preferred as standards for the shapes, dimensions and geometrical tolerances of the screws. Needless to say, if the outer diameter of the ball screw shaft 12 is higher in accuracy, then its outer diameter may be set as the standard. When it is desired to fix the bearing 36 to profiles 28 provided between the ball-screw splines 26 using balls 32, the diameter of each ball 32 may suitably be selected to adapt to the accuracy of processing of the two.

On the other hand, when the ball screw shaft 12 is fixed to the motor 20, male screws 40 are provided on the outer periphery of the ball-screw splines 26 so as to correspond to a rotor 38 as shown in FIG. 4, and stoppers 42 are attached to the motor 20 in a manner similar to the method for fixing the ball screw shaft 12 to the bearing 14, to thereby fix the ball-screw splines 26 and the rotor 38. In order to cause the rotor 38 to correspond with the stator 44 of the motor 20 at a predetermined position, a bearing 46 is fixedly provided outside of the stoppers 42, in accordance with a method similar to the fixing method of the rotor 38. A driving force of the motor 20 is transmitted to a ball-screw bush 72 (see FIG. 2) through the ball screw shaft 12. Further, the rotational motion of the ball screw shaft 12 is converted into a linear motion to thereby displace the table 16.

The first embodiment of the actuator according to the present invention is basically constructed as described above.

A structure made up of a combination of a table 16 and a frame 18 will next be described as another embodiment with reference to FIG. 6.

Respective pairs of grooves 48, each shaped substantially in the form of a letter T, are provided on both sides of a direct-acting guide 23 disposed on both sides of each of groove-like openings 22 defined in the frame 18. Respective pairs of guides 50, each of which serves as a rail for guiding the table 16, are fitted and inserted into corresponding grooves 48. Each of the guides 50 is shaped substantially in the form of a letter T, so as to be fitted into the groove 48. Further, V-shaped grooves 50, are respectively defined in portions of the guides 50, which guide the table 16. Bearings, e.g., roller or bearings 50b can be provided as shown in FIG. 6, such that the slide table 16 can be slidably moved with respect to the guides 50.

Longitudinally-extending rubber (e.g., a conductive rubber) contacts 54, each of which is used to supply power to the table 16 from power lines 52 provided within the frame 18, are provided inside one of the groove-like openings 22. The rubber contacts 54 are conductively connected with corresponding contacts 56 attached to the table 16 through either brushes or electricity-conductive cam followers, so as to effect the supply of power to the contacts 56 of the table 16. Further, either a light-emitting/light-receiving diode 58 or other communication device for transmitting signals to and receiving signals from the table 16 is provided inside the other of the groove-like openings 22. Either a photodiode 60 or other communication device for effecting optical communications, microwave communications and spread spectrum communications (which are excellent in resistance to noise in particular) over either the light-emitting/light-receiving diode 58 or the other communication device is attached to the table 16. A pneumatic path space may be used as a communication path for such communications. The power supplied to the contacts 56 of the table 16 is supplied thereto by a connector 64 provided on the upper surface of the table 16. The connector 64 may be any standardized connector such as a DIN connector. The angle of the connector may be varied through an angle of 90°. Further, the photodiode 60 is electrically connected to the connector 64 and a connector 65.

The turning angle of the ball screw shaft 12 is detected by an encoder 66 attached to one end of the ball screw shaft 12 (see FIG. 2). The encoder 66 may preferably comprise either an absolute type encoder or an absolute-signal output type integral encoder using an integrating counter memory. The encoder 66 has a sensor signal processing circuit, a serial signal generating circuit, etc. all of which are not shown.

A controller 68 disposed adjacent to the motor 20 comprises a driver module, a control module and a communication interface (not shown), depending on the function of the controller. The electrical connection between the communication interface and an unillustrated external device is made by connectors 70a and 70b.

The driver module has a driver for driving the motor 20, and a driver controller for controlling the drivers on an integral or united basis. Incidentally, the driver is used to effect a PWM and a digitally-controlled inverter control.

The control module controls or manages an actuator operation program, and transmits a position command or instruction and a speed instruction, or other drive control instructions, to the driver module. Further, the control module monitors signals fed back from the motor 20 and respective components of the driver module.

The communication interface provides mutual communications between a communication system and the control module via a serial or parallel interface. The communication system can be a LAN or an external controller, a PC (Programmable Controller/Personal Computer), a PLC (Programmable Logic Controller), or other types of computers, an Ethernet, a token ring, a MAP, a PC, a LAN, a LON (Local Operating Network), a WAN, an OSI, etc. The serial interface may comprise a RS232C and a RS422, or an interface dedicated to a GP-IB, a BCD and a Centronics parallel LAN. The parallel interface may comprise a high-speed optical LAN of 100-Mbps or the like, a Gateway, etc. The entire software structure is analyzed and constructed by an object oriented system or by programming. Further, each of the software, data, logic, or hardware structures is set as a recursive structure.

The respective components of each controller 68 may be integrally formed to realize a reduction in size. Alternatively, the components may be so constructed that they can be separated into various functions and held in common to many kinds of actuators, in order to improve general-purpose properties and realize a reduction in cost. For example, the control functions of the control module may be fully digitalized or semi-digitalized using an ASIC, a one-chip multi CPU, a DSP or the like, so as to realize both high function and low cost. Further, a complex control using a counterbalance set on a pneumatic actuator and a belt pulley, a cylinder air balance set on a belt pulley, a double-velocity air balancer, a multiaxis control using an endeffect, a force control, a position/velocity control, an XYZ, a θ coordinate, etc., and a device control using a conveyor, a turntable, an index table, a lifter, etc. can be performed simultaneously or integrally, along with simultaneous or integral control of various induction motors, an AC servomotor, a DC servomotor and a stepping motor, by switching a predetermined software in advance or in the course of operation as needed, thereby making it possible to further improve function and reduce cost. If the above-described system configuration is established, a self-decentralizing system can be achieved by using a CIM/FA intelligent system.

If a decision is made on motors to be controlled and corresponding interface formats based on impedances, circuit configurations or the like, and an identification memory using a data carrier, bar codes, ID tags or the like to thereby automatically cope with such a process via software, it is then possible to eliminate or greatly reduce labor cost and provide intelligent functions by constructing either a network or a line. Further, signals may be simultaneously transmitted using a power supply line connected to a motor or the like, to eliminate extraneous conductors or wires. An active noise control may be performed as a noise countermeasure for the actuator. In addition, attitude and rotational controls may be carried out by a triangular-pole type piezo-resonant (three dimensional) gyroscope.

A casing for the encoder 66 and the controller 68 is used in common with the frame 18. However, the casing and the frame 18 may be separate from each other depending on the construction of the actuator. In this case, the casing is fitted on the frame 18 by circular or polygonal fittings, or by engagements, pins or the like. Further, the transfer of electricity and signals, and the couplings between a bus, a LAN and a sensor or the like are also performed by connectors. In addition, fitting and connections between the two are effected simultaneously, and they are fixed together by caulking or welding using electron beams or the like. Alternatively, the controller, the motor, etc. may be shaped respectively in the form of modules, and may be added or removed as needed.

A description will next be made of a case wherein a timing belt is used as a power transmission section to drive the table.

Figure 7:
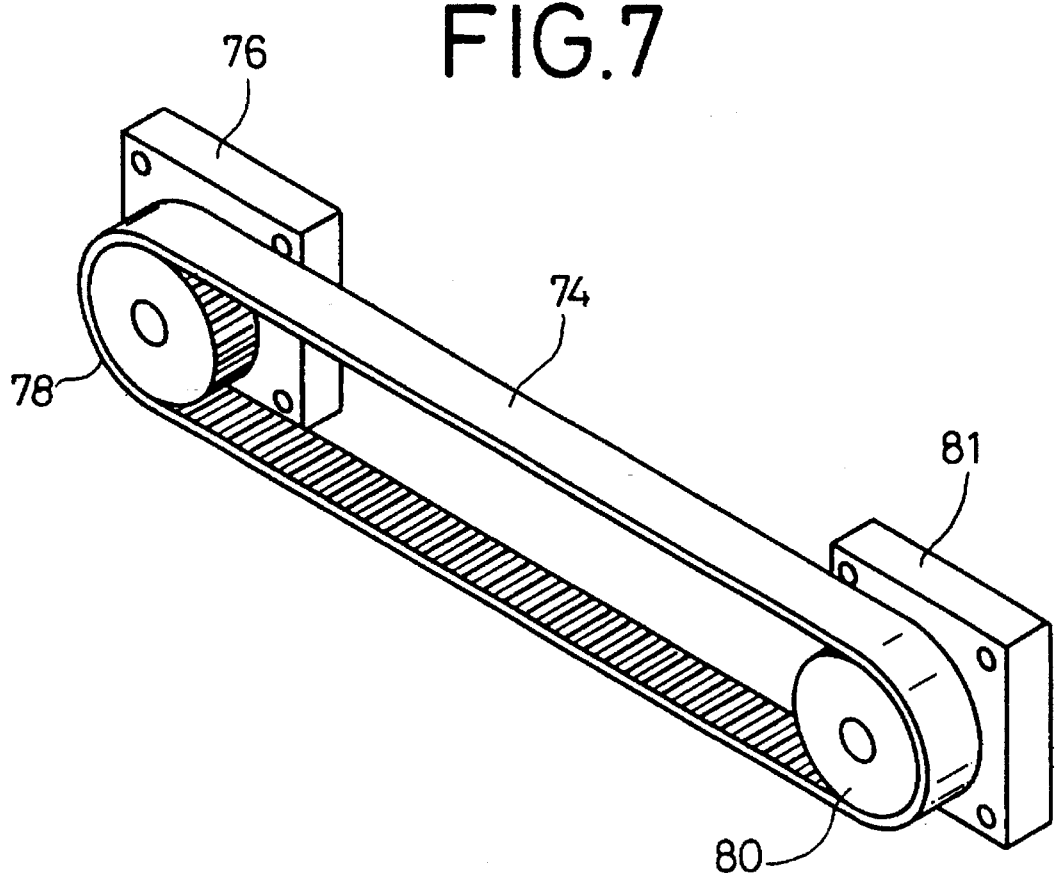
FIG. 7 is a perspective view showing a further embodiment of an actuator according to the present invention, which illustrates the manner in which a timing belt is directly driven by a motor.

FIG. 7 is a view for describing the manner in which a timing belt 74 is directly driven by a motor 76. A motor 76 for driving the timing belt 74 has a rotor which is formed integrally with a pulley 78 for engagement with either the timing belt 74 or a steel belt having synchronizing holes therein for preventing shifting of the belt. An encoder 81 is attached to another pulley 80 so as to detect the rotation of the motor 76.

Figure 8:
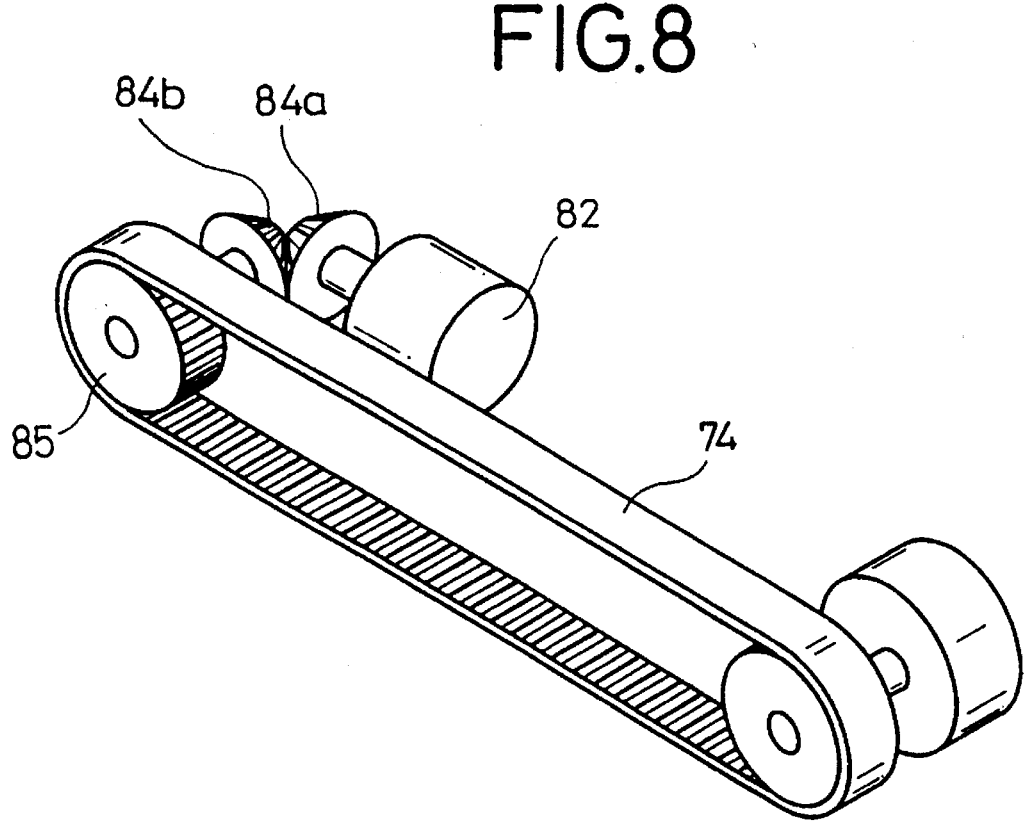
FIG. 8 is a perspective view showing a still further embodiment of an actuator according to the present invention, which illustrates the manner in which helical gears are driven by a motor, and wherein a timing belt is driven by a pulley.

In a further embodiment shown in FIG. 8, helical gears 84a and 84b of a motor 82 are operated to cause a pulley 85 to drive a timing belt 74. In this case, the helical gear 84a is formed integrally with a rotor of the motor 82. The remaining helical gear 84b is also formed integrally with a pulley 80. Further, rigidity and squareness of the arrangement can be enhanced by forming a bearing integrally with a motor casing.

Furthermore, FIGS. 9 through 13 respectively show embodiments in which a biomotor is used as an alternative to the motor 20 and the ball screw shaft 12 to drive the table 16.

Figure 9:
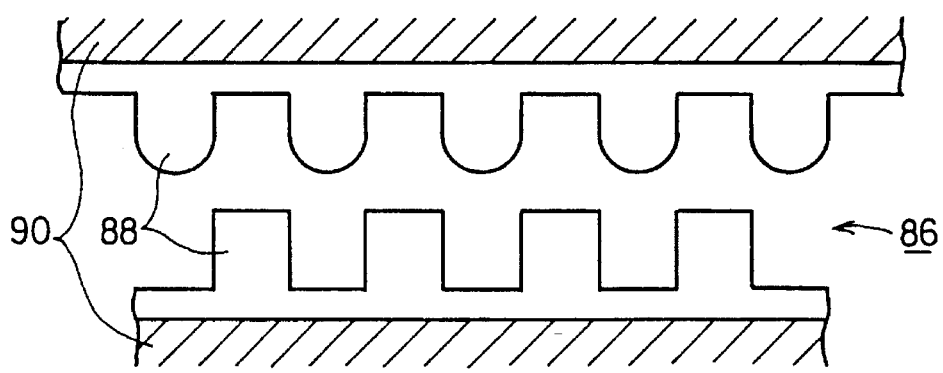
FIG. 9 is a view for describing the principle of a biopseudo linear actuator employed in a still further embodiment of an actuator according to the present invention.

FIG. 9 is a view for describing the principle of a biopseudo linear actuator. Patterns 88, which interact on each other by a muscle filament and a flagellum motor, are implanted on pseudo biological materials or pseudo biosubstances 90. The pseudo biosubstances 90 form linear shapes, cylindrical surfaces, disc shapes and disc surfaces. Further, the pseudo biosubstances 90 produce linear and rotational motions. A linear electromagnetic type linear actuator may also be used as the biopseudo linear actuator.

Figure 10:
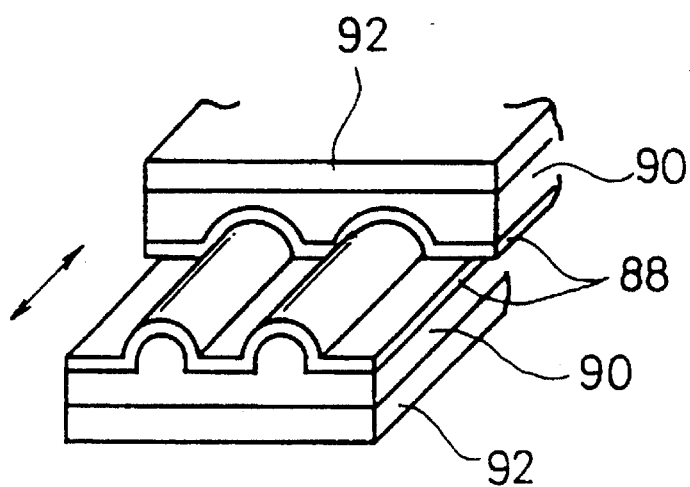
FIG. 10 is a partly-cut perspective view illustrating the manner in which pseudo biosubstances and patterns have been mounted on actuator bodies, each used as a still further embodiment of an actuator according to the present invention.

FIG. 10 shows the manner in which the pseudo biosubstances 90 and the patterns 88 have been mounted on actuator bodies 92 respectively.

Figure 11:
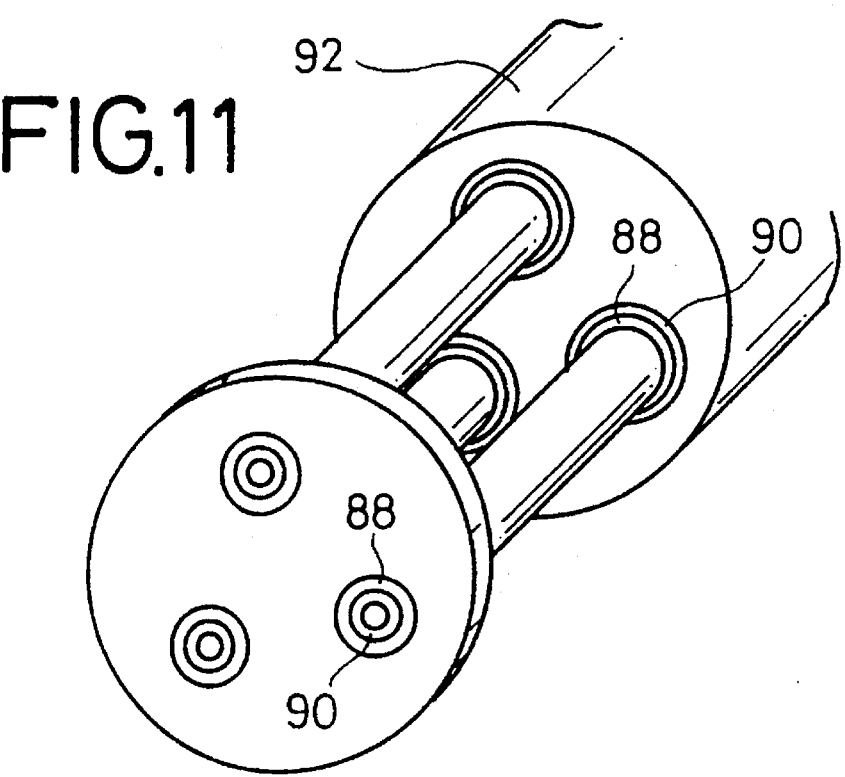
FIG. 11 is a partly-cut perspective view showing a still further embodiment of an actuator according to the present invention, which illustrates the manner in which pseudo biosubstances and patterns have been provided in a body of the actuator.

FIG. 11 is a view similar to FIG. 10 and illustrates an actuator shaped in the form of a cylinder.

Figure 12:
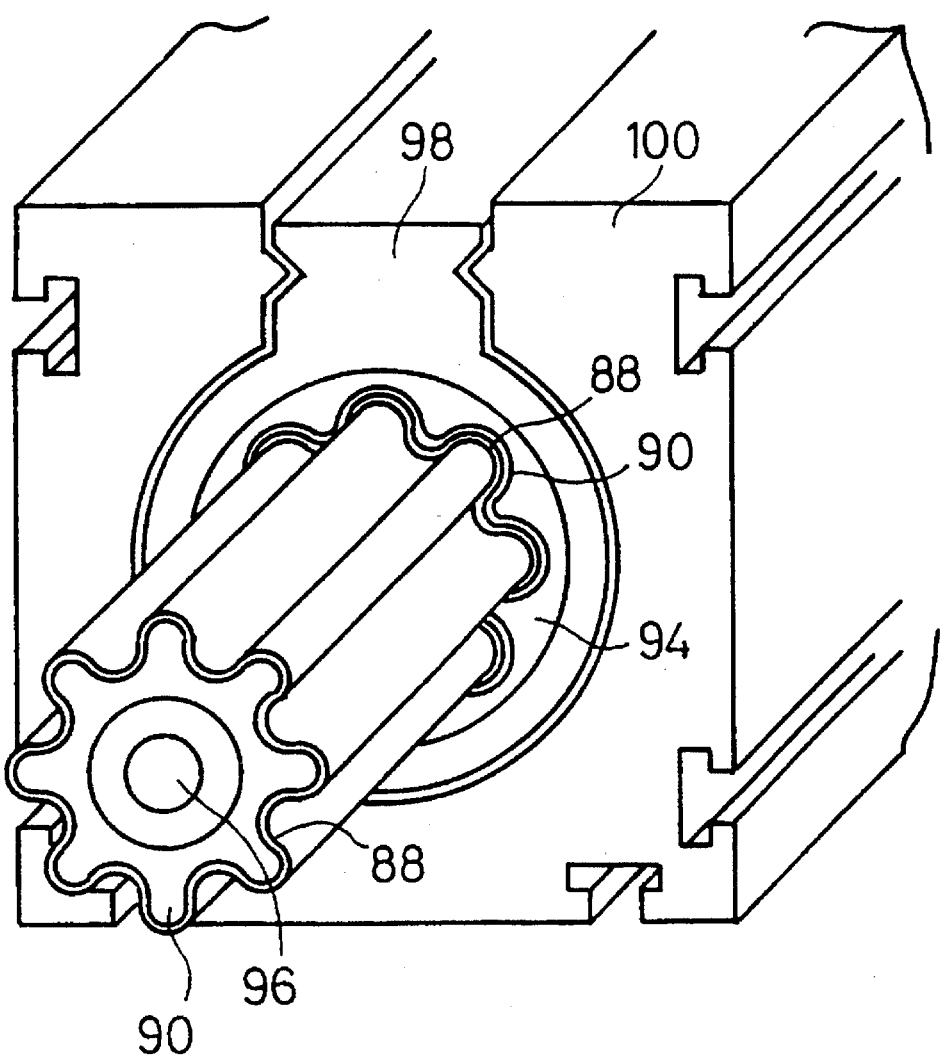
FIG. 12 is a partly-cut perspective view showing a bio-actuator corresponding to a still further embodiment of an actuator according to the present invention.
Figure 13:
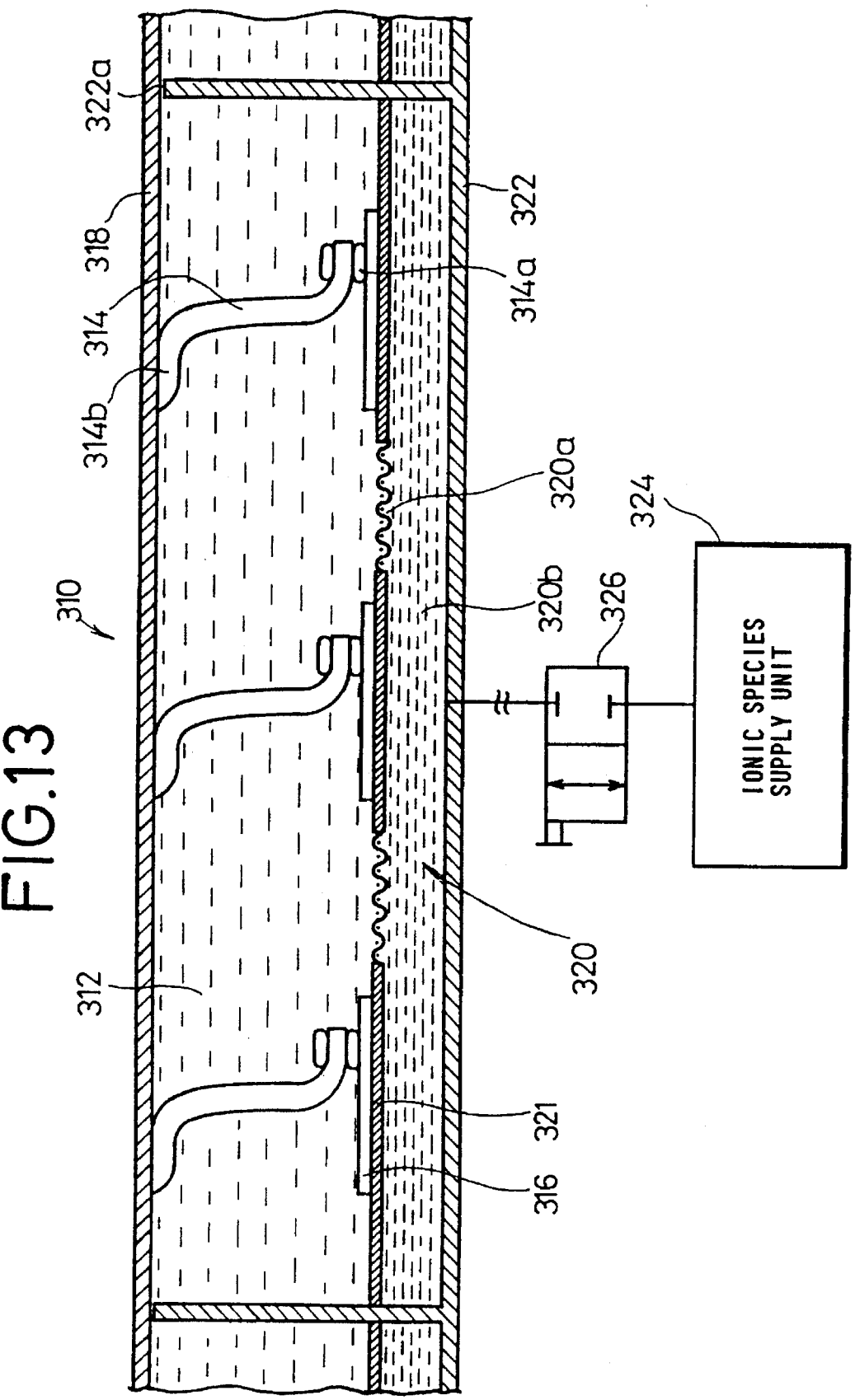
FIG. 13 is a schematic vertical sectional view showing a bioactuator illustrative of a still further embodiment of an actuator according to the present invention.

FIG. 12 illustrates an actuator wherein a pseudo biosubstance 90 and a pattern 88 are provided to drive a table 98 fitted in an actuator body 100. A bioenvironment setting means 94 and active substance introducing portion 96 are provided within the pseudo biosubstance 90, and a means is provided for supplying energy to the pseudo biosubstance 90. The energy supplying means comprises a system for introducing biochemical energy substances and blood which exist in a living body or organism, an intravital pseudo environment, or a uniform environment and in their peripheries and discharging them therefrom. The energy supplying means also includes a system for supplying ATP (adenosine triphosphate) energy from a biochemical energy circuit such as an intracellular portion, and supplying ATPase (adenosine triphosphatase) energy to thereby hold the activation of the pseudo biosubstance 90. The pattern 88 is produced by a bioproduction method using a DNA process or a micromachining method. A detailed description will now be made below of a specific drive unit structure of the actuator body shown in FIG. 12, with reference to FIG. 13.

An actuator 310 comprises a solution section 312, an energy supplying means and an ATP regenerating means, both of which exist in the solution section 312 in a diffused state. Myosins 314 and actins 316, both of which construct sarcomere structures corresponding to moving means are also provided. In addition, a movable member 318 for fixing a tail structure 314b of each myosin 314, a fixing member 321 for fixedly securing one side surface of each actin 316, and a controlling means are also included.

The solution section 312 is surrounded by a wall member 322 from three directions. The movable member 318 is slidably placed on the end surfaces 322a of the wall member 322 from the remaining one direction. The movable member 318 makes use of a material extremely light in weight, such as silicon, a fiber or the like to enhance the efficiency of conversion of biochemical energy into kinetic energy.

Each moving means comprises the myosin 314 and the actin 316 which form the sarcomere structure. The myosin 314 has a head structure 314a and the tail structure 314b, which is fixed to the movable member 318. One side surface of each actin 316 is secured to the fixing member 321 oppositely from a fixing surface of the movable member 318, and whose peripheral portions are fixed to the wall member 322. The myosin 314 and the actin 316 each is made up of a myofibril-derived muscle protein having a thickness of 1 µm or so in diameter, and which forms a striated muscle in a biological organism. The myosin 314 has a molecular weight of 450000 or so and corresponds to a giant molecule having a diameter of 12 nm and a length of 42.9 nm or so, whereas the actin 316 has a molecular weight of 42000 or so and corresponds to a protein having a diameter of 8 nm and a length of 37.5 nm or so. Incidentally, the genus, species and the like of the biological organism to be used are not limited, but may be selected according to the purpose and application. A medical micromachine employed in, for example, a human organism may preferably utilize human-derived proteins to avoid symptoms such as rejection of the organism, or antigen-antibody reactions, etc.

The energy supplying means comprises a hydrolase system which exists in the head structure 314a of the same myosin 314 as that forming the moving means, and has an ATPase (adenosine triphosphatase) and an ATP which exists in a diffused state in the solution and stores biochemical energy therein in the form of phosphoric compounds. The ATP is hydrolyzed into an ADP and inorganic phosphorus, thereby supplying the energy to the moving means.

The ADP produced by the energy supplying means is reproduced or regenerated in the following manner. A chemical energy supplied through an ionic species is converted into biochemical energy in the form of phosphoric compounds by the ATP regenerating means and the controlling means, so as to be stored in the ATP. A desired amount of ATP is supplied to the energy supplying means.

The ATP regenerating means comprises an ADP which exists in a diffused state in the solution section 312, ionic species such as $Na^+$, $K^+$, $Ca^+$, $Mg^+$, $H^+$, etc., each having chemical energy in a charged state and in an activated or energized state, creatine phosphate and creatine kinase systems corresponding to ATP regenerative enzymes, and coenzymes thereof. Incidentally, phospho-enolpyruvic acid and pyruvate kinase systems and coenzymes thereof may also be used as the ATP regenerative enzymes.

Further, there is also supplied an ionic species which is required to supply energy to the moving means from the energy supplying means, and effect the regeneration of ATP by the ATP regenerating system. Moreover, a controlling means for controlling the amount of ionic species to be supplied comprises a biopump 320 made up of functional membranes 320a and a high-concentrated solution section 320b disposed in a movable member 318, an ionic species supply unit 324 capable of selectively supplying special ionic species in predetermined amounts depending on a reduction in concentration of the ionic species in the solution section 320b, and a valve 326. Each functional membrane 320a employs an endoplasmic reticulum membrane capable of actively balancing the concentration between the solution section 312 and the high-concentrated solution section 320b. However, a regenerative endoplasmic reticulum membrane, a sub-chloroplast, a phosphatid double membrane or the like may also be used, each having the same function as that of the endoplasmic reticulum membrane.

The controlling means effects a pH-concentration adjustment for suitably activating the energy supplying means and the ATP regenerating means, and controlling addition of the coenzyme.

Thus, when biochemical energy is converted into kinetic energy by the actuator 310, the myosins 314 and the actins 316, each of which is capable of obtaining a desired kinetic energy and whose respective solids exhibit uniform biological behaviors, are first placed in predetermined positions respectively. At the same time, the functional membrane 320a is selected and set taut for providing a suitable solution state to obtain the desired kinetic energy. The solution section 312 and the high-concentrated solution section 320b can be maintained in an unreactive state while each myosin 314 remains inactivated, as well as being brought into a state of biological activity, i.e., a state of solution free of life loss. Thus, the resultant state of the solution may be defined as the ground state.

The valve 326 is next opened to cause the ionic species supply unit 324 to diffuse an ionic species, a pH control factor, an ATP, etc. which are held in a highly concentrated solution state A into the high-concentrated solution section 320b, thereby obtaining a highly concentrated solution state B. The concentrated solution state B is actively brought into the solution section 312 through each functional membrane 320a, so that a solution state C having a concentration suited to start the movable member 318, (i.e., the table 98) can be obtained.

In other words, when the solution state C is obtained, each myosin 314 forming the energy supplying means is first linked to an ATP having biochemical energy stored therein in the form of phosphoric compounds. Then, the ATPase (adenosine triphosphatase) of the hydrolase system, which exists in the head structure 314a of the ATP, is hydrolyzed into ADP and Pi. The head structure 314a of each myosin 314 is brought into contact with the surface of the actin 316 as a result of the biochemical energy produced upon hydrolysis. Thereafter, the head structure 314a begins slidings on the surface of the actin 316 along a predetermined direction. Since each of the myosin 314 and the actin 316 comprises a biological component, and since the solution in the solution section 312 is in a pseudo intravital environment, their behavior depends on the homeostasis keeps the intravital environment in a given state. That is, such a behavior converts an ATP into kinetic energy thereby enabling the biological organism to be raised to an energy-storage allowable threshold value, (i.e., a biochemical energy existing in vivo) and discharging such energy to the outside of the organism.

Then, the APT regenerating means, which exists in the solution section 312, regenerates the ADP produced in the solution section 312 by hydrolysis to thereby produce the ATP, which is in turn supplied as energy again. This behavior creates a state of the ADP is diffused into the solution section 312 and incorporates therein an ionic species such as $Na^+$, $K^+$, $Ca^+$, $Mg^+$, $H^+$, etc., which are supplied under active transport from the high-concentrated solution section 320b, each ionic species having a chemical energy in a charged state, and being in an activated or energized state. The creatine phosphate and the creatine kinase systems correspond to ATP regenerative enzymes and coenzymes thereof, and the chemical energy is stored in the ATP as a biochemical energy in the form of phosphoric compounds.

Further, when the above series of behaviors are successively performed, the solutions which exist in the high-concentrated solution section 320b and the solution section 312 are brought into equilibrium when the valve 326 is closed. As a result, the ionic species such as $Na^+$, $K^+$, $Ca^+$, $Mg^+$, $H^+$, etc. each having a chemical energy energized under a charged state, are inactivated and the energy supplied to the ATP regenerating system is lost. Therefore, the solution is returned to a ground state, so that the head structure 314a of each myosin 314 stops sliding and is returned to the original position.

At this time, the movable member 318, to which the tail structure 314b of each myosin 314 has been fixed, moves according to the distance that each myosin 314 be slid.

On the other hand, when the valve 326 is in an open state, the myosin 314 continues to slide and the movable member 318 thus also continues moving.

A description will next be made of an arrangement in which the actuators constructed as described above are incorporated.

Figure 14:
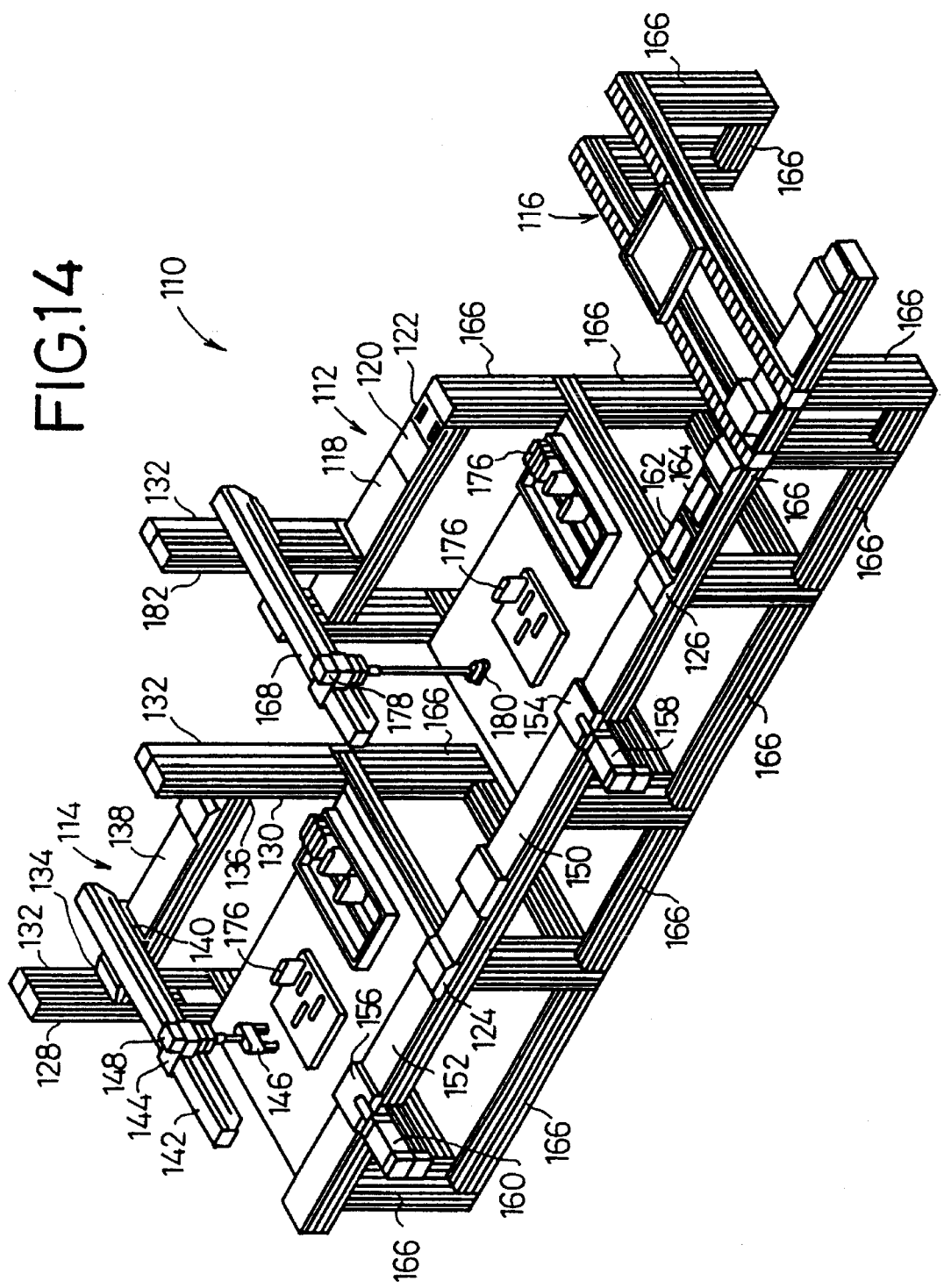
FIG. 14 is a perspective view showing an arrangement in which actuators according to the present invention have been incorporated.

Referring to FIG. 14, the arrangement 110 of actuators comprises a first section 112 and a second section 114, each placed side by side, wherein the first section 112 depends from a working step. A belt conveyor 116 is placed in juxtaposition with the first section 112.

The first section 112 is provided with a motor box 120 and a controller 122 having a display, both of which are attached to one end of the actuator 118, so as to be flush with an upper surface of the actuator 118. Owing to the fact that the motor box 120 and the controller 120 are formed flush with the upper surface of the actuator 118, the motor box 120 and the controller 122 are compatible with other members when they are attached thereto. Further, since both the motor box 120 and the controller 122 are compact in configuration, space can be effectively utilized. Thus, other motor boxes 124 and 126, etc. as shown in the drawing can be formed so as to be flush with the upper surfaces of the actuators disposed in the arrangement 110.

On the other hand, the second section 114 is constructed so that balancers 132 placed side by side with actuators 128 and 130 are respectively provided in a vertical facing relationship, wherein both ends of an actuator 138 are connected to sliders 134 and 136 for the actuators 128 and 130 and the balancers 132, which are placed side by side with one another. The actuator 138 is disposed substantially at a right angle to the actuators 128 and 130 and the balancers 132. Further, the actuator 138 is coupled to the actuators 128 and 130 and the balancers 132, so as to be held in a substantially horizontal position. An actuator 142 is coupled to a slider 140 for the actuator 138. A cylinder 148, having a rod whose leading end portion is connected to a mechanical hand 146, is coupled to a slider 144 for the actuator 142. The first and second sections 112 and 114 are connected to each other, and actuators 150 and 152 extending in the longitudinal direction thereof are connected side by side to each other. Cylinders 158 and 160, having respective positioning cylinder rods, are coupled to corresponding sliders 154 and 156 for the actuators 150 and 152.

Next, a belt conveyor 116 is connected side by side to the first section 112. Further, programming keyboards 162 and 164, each of which serves as an input/output device of a control system, are attached to a portion where the belt conveyor 116 is connected to the first section 112. Each of the programming keyboards 162 and 164 is detachably positioned on one of concave columnar members or columnar members 166. Various devices are incorporated into the arrangement 110. Described specifically, various actuators 168, 138, 142, 128, 130, 150 and 152, balancers 132, cylinders 158, 148 and 160, a mechanical hand 146 and a belt conveyor 116, and the like, can be controlled by the control system. Various controllers, processors and circuits for transmitting signals such as an optical signal, an electric signal, a fluid-pressure signal, etc., all of which form the control system, are accommodated within their corresponding actuators and columnar members 166. These components have already been described in connection with the actuator disclosed in Japanese Patent Application No. 4-81159. The respective sections and the conveyor are combined via indexes and turntables.

A description will next be made of a case wherein the actuator arrangement 110 includes a plurality of steps in its entirety, and serves as an independent production line.

Figure 15:
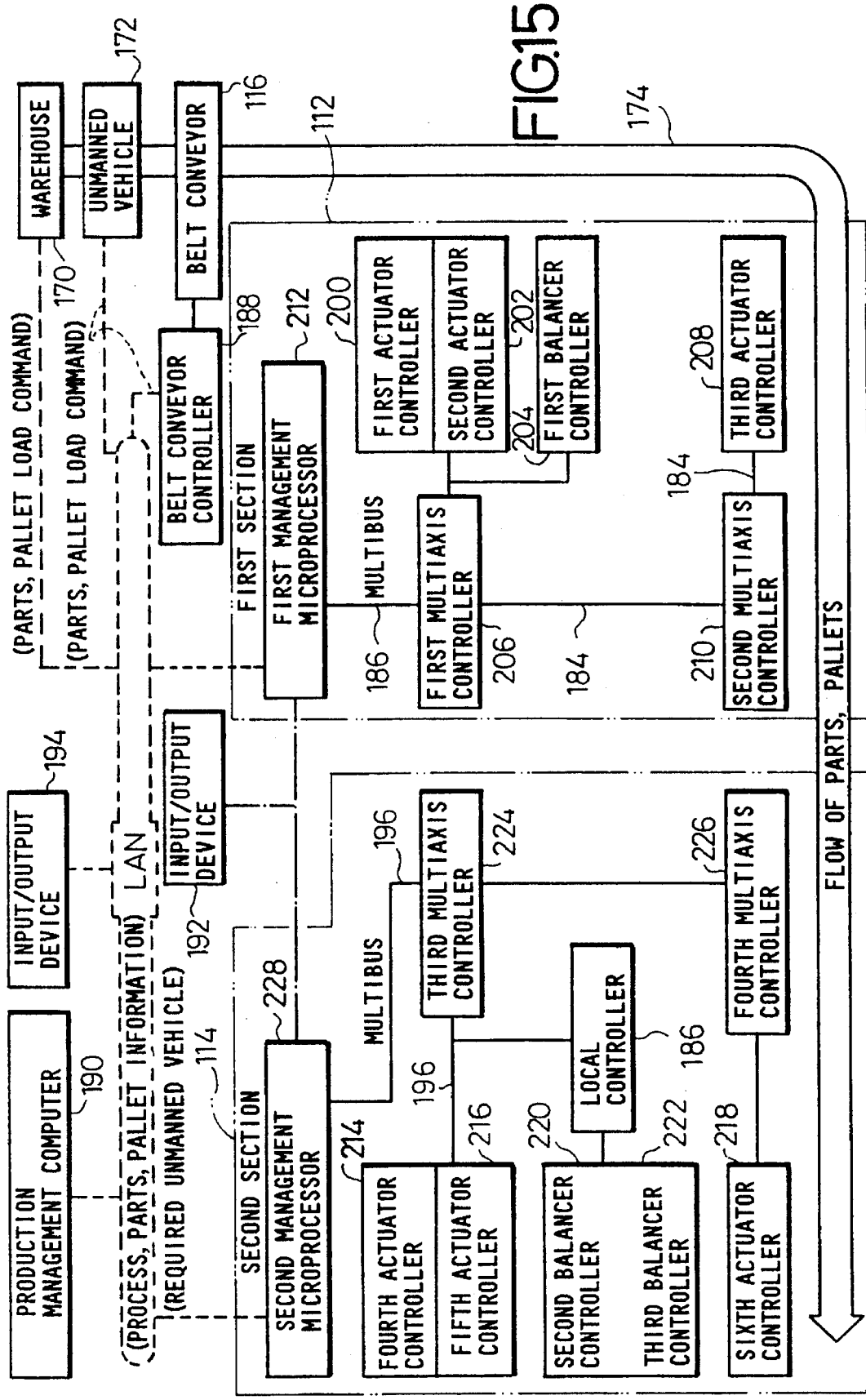
FIG. 15 is a control block diagram for describing the operation of the arrangement having the actuators shown in FIG. 14 incorporated therein.

As shown in FIG. 15, a parts pallet 174 having an unillustrated ID module is conveyed from a warehouse 170 by means of an unmanned vehicle 172 and a belt conveyor 116. The parts pallet 174 is delivered to the first section 112 of the arrangement 110, and subjected therein to predetermined steps. Each of the workpieces 176 also has an ID module in the same manner as described above. Thereafter, an unillustrated conveying means conveys the parts pallet 174 to a second section 114. At the second section 114, the parts pallet 174 is subjected to predetermined steps, and thereafter to other steps on a predetermined production line. Further, the parts pallet 174 is conveyed and thereby subjected to other steps.

A description will now be made of a case wherein respective sections of the actuator arrangement 110 serve as independent production lines.

Referring to FIG. 15, the actuator 118 is controlled by a first actuator controller 200. The actuator 168, a cylinder 178 and a suction pad 180 are controlled by a second actuator controller 202, whereas an actuator 182 and the balancer 132 are controlled by a first balancer controller 204. Further, the first actuator controller 200, the second actuator controller 202, and the first balancer controller 204 are electrically connected via a multibus 184 and integrally controlled as a single working unit by a first multiaxis controller 206. Furthermore, the actuator 150 and the cylinder 158 are controlled by a third actuator controller 208, and electrically connected via the multibus 184 and integrally controlled as a single working unit by a second multiaxis controller 210.

Thus, the integral control of the first section 112 in the arrangement 110 is performed by a first management microprocessor 212 electrically connected to the first multiaxis controller 206 and the second multiaxis controller 210. Further, the section 112 is controlled via a LAN using an electric signal, an optical signal, or a radio-communication or the like.

Similarly, the actuator 138 in the second section 114 of the arrangement 110 is controlled by a fourth actuator controller 214. The actuator 142, the cylinder 148 and the mechanical hand 146 are controlled by a fifth actuator controller 216. The actuator 152 and the cylinder 160 are controlled by a sixth actuator controller 218. The actuator 128 and the balancer 132 are controlled by a second balancer controller 220. And the actuator 130 and the balancer 132 are controlled by a third balancer controller 222. In order to move the actuator 138 in a substantially vertical direction while being held horizontally, the second balancer controller 220 and the third balancer controller 222 are electrically connected to a local controller 186 to effect an integrated synchronous control. The fourth and fifth actuator controllers 214 and 216 and the local controller 186 are electrically connected via a multibus 196 and integrally controlled as a single working unit by a third multiaxis controller 224. Thus, the integral control of the second section 114 is also effected by a second management microprocessor 228 electrically connected to the third multiaxis controller 224 and a fourth multiaxis controller 226. Further, the section 114 may also be controlled via a LAN using an electric signal, an optical signal or a radio communication. The first through sixth actuator controllers can also be operated as balancer controllers, respectively, whereas the first through third balancer controllers can also be operated as actuator controllers.

The belt conveyor 116 is controlled by a controller 188 for the belt conveyor, and the unmanned vehicle 172 and the warehouse 170 are controlled by an illustrated control device and an unillustrated control system respectively.

The first management microprocessor 212, the second management microprocessor 228, and the controller 188 for the belt conveyor and respective control devices (not shown) for both the unmanned vehicle 172 and the warehouse 170 are respectively constructed in a LAN network using an electric signal, an optical signal, a radio signal, a spectrum diffusion communication, or the like, so that information can be mutually and freely transferred therebetween. It is therefore possible to construct an integrated control system suitable for use in the actuator arrangement 110 operated as an independent production line.

Other production management, information, communication and control systems, as well as control systems for an actuator structure 110 operated similar to the above, are electrically connected to the LAN network, thereby providing a large-scale integrated production management system. For example, a production management computer 190 operated as a host management computer, such as an FA, a CIM and a CAD/CAM/CAE concurrent system, may be electrically connected to the LAN network so as to form part of the network. In this case, either a program procedure or a program edit is performed on a real time basis so that an ordering, a scheduling or process control, a cost control, an improper-value control, a quality control, a stock control, a physical distribution management, assembling, processing, and conveying procedures are executed in accordance with a system controlled by the CIM. Accordingly, processes for making orders, and controlled systems or objects such as respective actuators, sensors, pallets, pallet stopper cylinders, ID control devices, serial control transmission devices, robots, control devices, etc., all of which are employed with the execution of the above items, are operated in accordance with the above processes. A virtual reality system, a three-dimensional graphic system or a multi-window EWS may be employed as the entire system comprised of an input/output device, a control device and a man-machine device for effecting these operations.

Input/output devices 192 and 194, such as the programming keyboards 162 and 164 or the like as shown in FIG. 14, are provided as a user interface for these systems. The input/output devices 192 and 194 can be freely connected to respective controllers, processors, computers, etc. through a general-purpose interface such as a RS232C, a RS422C or the like, a LAN using an electric signal, an optical coaxial communication, a radio signal, a multibus, Ethernet or a token link. Further, the input/output device or a general-purpose interface may be connectable to a host CIM computer, a controller, a processor, etc. In this case, entire control program processes such as editing, creation, alternation, downloading, uploading, input/output, etc., can be carried out by the respective controllers, processors, computers or the like, as well as by the host CIM computer. Further, an access can be arbitrarily effected on a controller, a processor or a computer. In this case, communications may be carried out between these components through a multibus and a LAN. However, the controllers, the processor and the computer may also be directly connected to each other through a network. Alternatively, they may be directly or indirectly connected to one another through a software based virtual network. Thus, overall control, and monitoring and operation of control information at a job site can be effected. Further, an independent discrete control, capable of maintaining the integrity of the entire system as it is, can be effected on respective works and process management, as well as providing an improvement in workability. This permits an improvement in flexibility of the entire system, and easily facilitates any required change in the system, as well as facilitating maintenance of the system and the production of many kinds products in small quantities.

Figure 16:
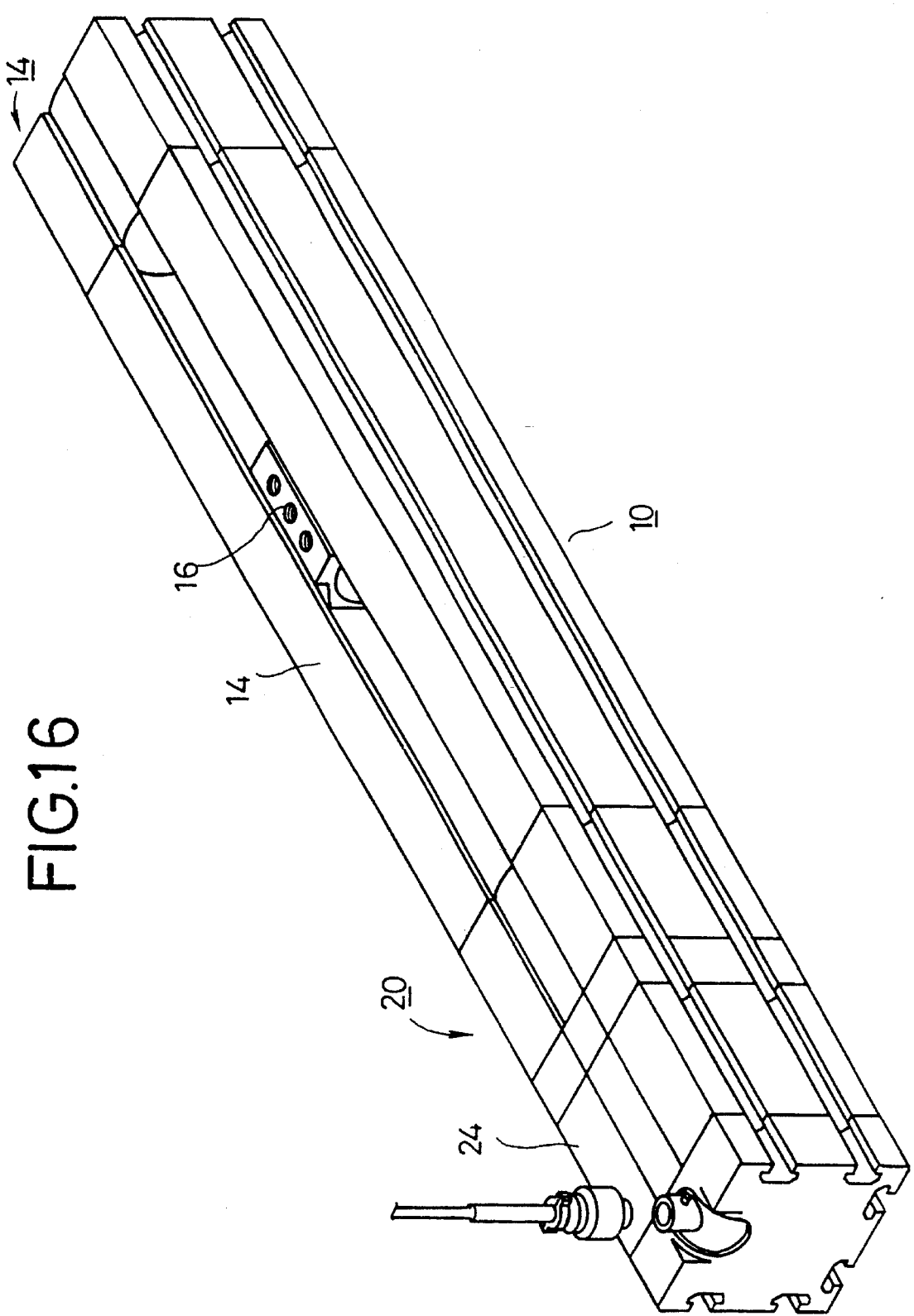
FIG. 16 is a perspective view illustrating a still further embodiment of an actuator according to the present invention.
Figure 17:
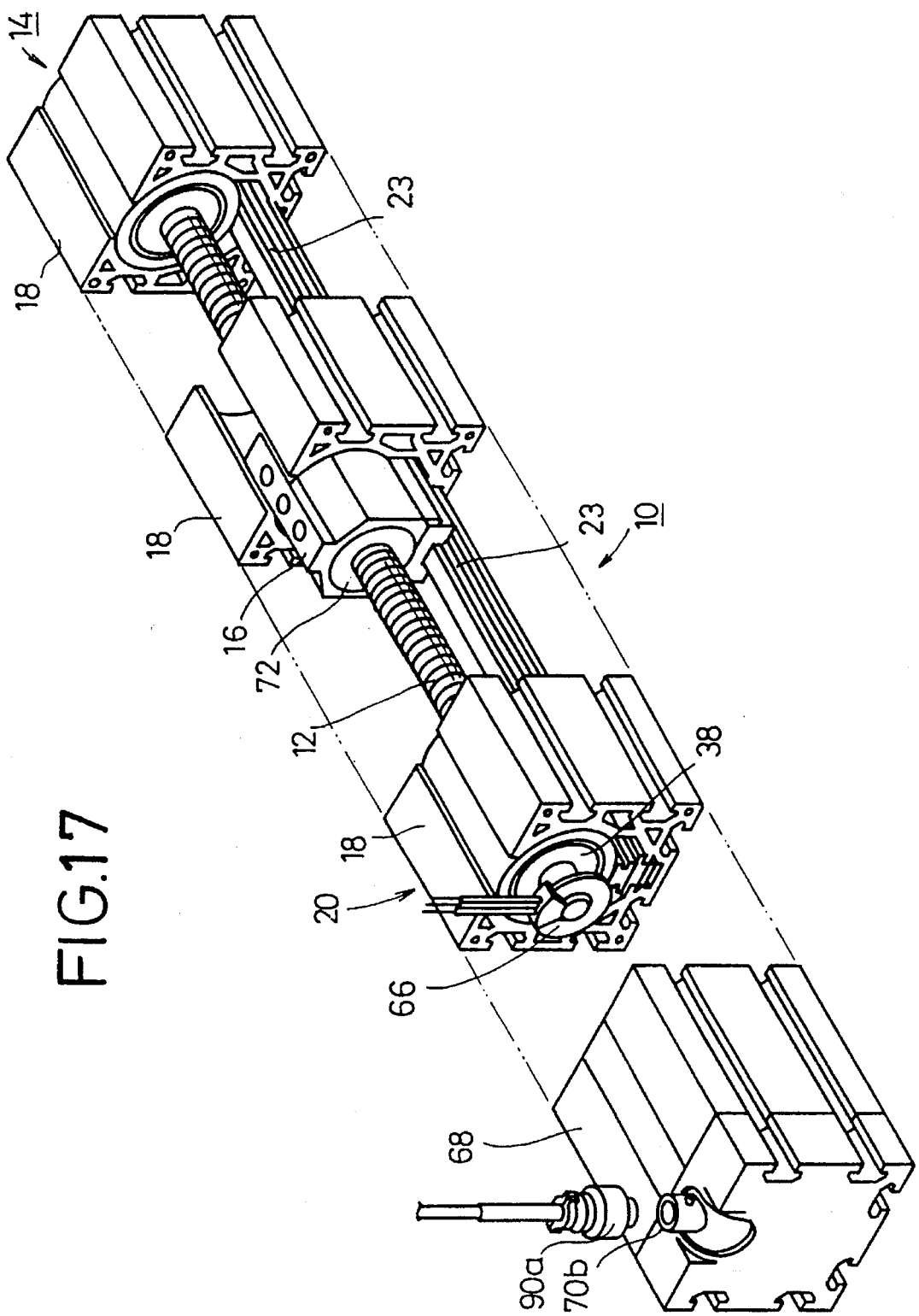
FIG. 17 is a partly-cut exploded perspective view illustrating the actuator shown in FIG. 16.

A still further embodiment of an actuator employed in an arrangement will now be shown in FIGS. 16 and 17.

This type of actuator is substantially identical to the actuator shown in FIG. 1. Therefore, the same structural elements as those in the actuator shown in FIG. 1 are identified by like reference numerals, and will not be described in detail. However, the present actuator differs in structure from the actuator shown in FIG. 1 in that a table is accommodated within an actuator frame, and direct-acting guides are also provided within the actuator frame.

Figure 18:
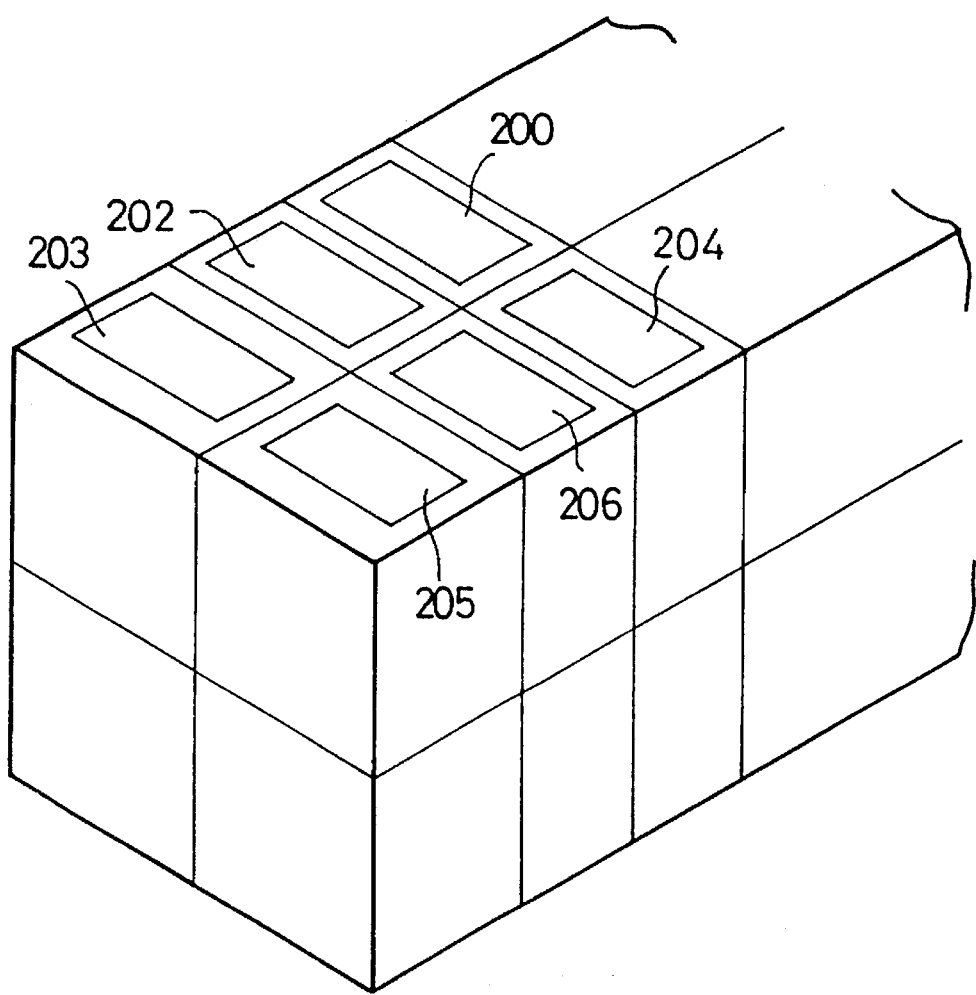
FIG. 18 is a perspective view for describing the shape of a controller employed in a still further embodiment of an actuator according to the present invention.

Further, the controller 68 shown in FIG. 2 may be constructed as a combination of respective functions, comprising a display section 200, an operation section 202, a data and program input section 204, a start and emergency stop button 206, an external communication control interface, a LAN interface 203, a power input section 205, etc. as shown in FIG. 18. Thereby, such elements can be positionally changed from a horizontal to a vertical direction or vice versa, or from an upward to a downward direction or vice versa, or from left to right or vice versa, and they can be positionally shifted or rotated to expose other surfaces thereof. The controller shown in FIG. 18 is shaped in the form of a cube, but may be shaped in the form of either a hexagon or an octagon. Further, the controller may be disposed between a plurality of adjacent actuators so as to control the actuators. Moreover, a power source used for the controller may be electrically series-connected to the controller.

INDUSTRIAL APPLICABILITY

According to the present invention, as has been described above, a rotating source can be easily and accurately made concentric with a rotatable shaft, by integrally aligning a feed screw shaft serving as a rotational and linear motion converting means with both the rotating source and the rotatable shaft.

An actuator can be reduced in size by forming pulley gears for a timing belt and a V belt integrally with the rotor of a motorized drive source.

Even when the direction of rotation is changed by means of helical gears, such helical gears can be formed integrally with a rotor of a rotatable drive source so as to eliminate coupling and provide a reduction in size.

Further, an arrangement for actuators, supporting actuators, or both can be formed integrally with a casing for a drive source, so as to provide a further compact configuration.

Thus, a rotational and linear bearing means for a drive source, a transmission gear and a slider can be reduced in number and enhanced in rigidity.

The arrangement, the drive source, the transmission gear and the slider can also be made compact by precision investment casting, metal pressing, extrusion, drawing or injection molding.

Moreover, an actuator using a pseudo biosubstance can be attached to a micromachine minimized in size, which operates bases on principles different from that of an instrument machine which has heretofore been considered, and in such a manner that the actuator can be driven by converting biochemical energy into kinetic energy.

Such a pseudo biosystem can bring about the advantage that a biochemical energy employed therein can be converted into a highly efficient kinetic energy.

We claim:

1. An actuator comprising:
    a feed screw shaft operatively connected at one end thereof to a rotor of a motor for converting a rotational motion of said motor into a linear motion to displace a slider and wherein said feed screw shaft is connected at an opposite end thereof to a bearing permitting rotational motion of said feed screw shaft, said feed screw shaft having ball-screw splines formed over a length thereof, wherein said feed screw shaft is connected with said rotor and said bearing such that a center of rotation of said feed screw shaft is aligned with a center of rotation of said rotor and a center of rotation of said bearing by a plurality of balls disposed in said ball-screw splines between said feed screw shaft and said rotor, and between said feed screw shaft and said bearing, respectively.

2. An actuator as claimed in claim 1, wherein said motor and said feed screw shaft are accommodated within a frame forming an outer frame.

3. An actuator as claimed in claim 2, wherein said frame has a groove-like opening defined therein and direct-acting guides are provided in the vicinity of said opening.

4. An actuator as claimed in claim 3, wherein grooves are provided on both sides of each of said direct-acting guides, and guides for guiding the slider are inserted into said grooves respectively.

5. An actuator as claimed in claim 4, wherein said slider is slidably moved along said guides by rollers interposed therebetween.

6. An actuator as claimed in claim 1, wherein said ball-screw splines comprise male threads provided on a periphery thereof.

7. An actuator as claimed in claim 6, further comprising stoppers threadedly engaged with said male threads of said ball-screw splines for securing said ball-screw shaft to said rotor at said one end, and for securing said ball-screw shaft to said bearing at said opposite end thereof, respectively.

* * * * *